United States Patent
Yoshimura

(10) Patent No.: US 11,326,233 B2
(45) Date of Patent: May 10, 2022

(54) MANUFACTURING METHOD OF IRON SOAP

(71) Applicant: NOF CORPORATION, Tokyo (JP)

(72) Inventor: Takeshi Yoshimura, Hyogo (JP)

(73) Assignee: NOF CORPORATION, Tokyo (JP)

(*) Notice: Subject to any disclaimer, the term of this patent is extended or adjusted under 35 U.S.C. 154(b) by 23 days.

(21) Appl. No.: 16/918,534

(22) Filed: Jul. 1, 2020

(65) Prior Publication Data

US 2020/0332396 A1    Oct. 22, 2020

Related U.S. Application Data

(62) Division of application No. 15/527,481, filed as application No. PCT/JP2015/082067 on Nov. 16, 2015, now abandoned.

(30) Foreign Application Priority Data

Nov. 18, 2014  (JP) .............................. JP2014-234065

(51) Int. Cl.

| | | |
|---|---|---|
| *C22C 33/02* | (2006.01) | |
| *C11D 9/00* | (2006.01) | |
| *C07C 53/128* | (2006.01) | |
| *C08K 5/098* | (2006.01) | |
| *C11D 1/04* | (2006.01) | |
| *C11D 17/06* | (2006.01) | |
| *C07C 51/41* | (2006.01) | |
| *B22F 1/105* | (2022.01) | |
| *B22F 1/10* | (2022.01) | |

(52) U.S. Cl.
CPC .............. *C22C 33/02* (2013.01); *B22F 1/105* (2022.01); *B22F 1/108* (2022.01); *C07C 51/412* (2013.01); *C07C 53/128* (2013.01); *C08K 5/098* (2013.01); *C11D 1/04* (2013.01); *C11D 9/00* (2013.01); *C11D 17/06* (2013.01); *C08K 2201/014* (2013.01)

(58) Field of Classification Search
CPC .................................. C22C 33/02; C11D 9/00
USPC ........................................................... 75/246
See application file for complete search history.

(56) References Cited

FOREIGN PATENT DOCUMENTS

| | | | |
|---|---|---|---|
| JP | S62120339 A | | 6/1987 |
| JP | H20178250 A | | 7/1990 |
| JP | H06504079 A | | 5/1994 |
| JP | H06271499 A | | 9/1994 |
| JP | 11323396 A | * | 11/1999 |
| JP | H11323396 A | | 11/1999 |

* cited by examiner

*Primary Examiner* — Weiping Zhu

(74) *Attorney, Agent, or Firm* — Muncy, Geissler, Olds & Lowe, PC

(57) ABSTRACT

A method of manufacturing an iron soap is disclosed herein. The method comprising the steps of: reacting, at a temperature equal to or lower than a crystal transition initiation temperature of the iron soap to be manufactured, between a straight-chain saturated fatty acid alkali metal salt aqueous solution having from 12 to 22 carbons and a trivalent iron salt aqueous solution with pH of 0.1 to 5.5 so as to prepare an iron soap slurry; and adjusting pH of the prepared iron soap slurry to from 0.1 to 6.0.

1 Claim, No Drawings

MANUFACTURING METHOD OF IRON SOAP

CROSS-REFERENCE TO RELATED APPLICATION

This application is a divisional of U.S. patent application Ser. No. 15/527,481, filed on May 17, 2017, in the United States Patent and Trademark Office, which claims the benefit of PCT/JP2015/082067, filed on Nov. 16, 2015, and this application claims priority of Application No. 2014-234065 filed in Japan on Nov. 18, 2014 under 35 U.S.C. § 119, the disclosure of which is incorporated herein in its entirety by reference.

BACKGROUND OF THE INVENTION

Field of the Invention

The present invention relates to a manufacturing method of an iron soap, and in particular, relates to: a manufacturing method of an iron soap which has high compatibility and dispersibility with respect to a thermoplastic resin and which is capable of suitably being used as a dispersant for a photodecomposition catalyst, an inorganic powder or the like. The manufacturing method is able to produce the iron soap in high yields.

Description of Related Art

A metal soap has been widely used in many fields such as a resin processing field, an electronic printing field, a powder metallurgy field, a cosmetic field, a coating material field, and a cement field. Examples of a currently practiced representative method of manufacturing a metal soap include a method of reacting a fatty acid with an inorganic metal oxide or with an inorganic metal hydroxide (direct method) or a method of reacting, in a water system, an alkali metal salt solution of a fatty acid or an ammonium salt solution of a fatty acid with inorganic metal salts (double decomposition method).

Among the metal soaps, an iron soap is used as a dispersant for a photodecomposition catalyst, an inorganic powder or the like, in the field of resin processing and powder metallurgy. Generally, the iron soaps are industrially manufactured by a double decomposition method of reacting an alkali metal salt solution of a fatty acid or an ammonium salt solution of a fatty acid with an inorganic iron salt in the water system, or by an exchange method of reacting a fatty acid and an iron alkoxide. In particular, in the resin processing field or the powder metallurgy field, a high dispersion is demanded and from such a view point, the iron soap obtained by the double decomposition method is suitably used.

For example, in the section of "Technical Problem" in Patent Literature 1, it is stated that the double decomposition method is unable to completely convert a stearic acid to an iron stearate, and thus, 7 to 10% of unreacted sodium stearate remains in the product. Further, there is a problem in that a structure of an iron (III) soap is unstable, and thus, hydrolysis occurs during double decomposition reaction, resulting in producing free fatty acids. There is a problem when fatty acid salts and free fatty acids are created, the purity of iron (III) soap decreases.

Therefore, the Patent Literature 1 describes a manufacturing method of manufacturing fatty acid iron salts by, after a saponification reaction between a fatty acid and an alkali hydroxide, reacting the resultant fatty acid alkali metal salt with an acidic iron salt to perform a double decomposition reaction, that is, a method of manufacturing fatty acid iron salts, which is characterized in that the saponification reaction and the double decomposition reaction are performed alternately at a temperature of 90° C. plural number of times by alternately adding the alkali hydroxide and the acidic iron salt to a reaction system in a large excess to the fatty acid plural number of times so that unreacted fatty acids decrease. It is also mentioned that the fatty acid iron salts which have a good color tone, fine powder, and a high purity are obtained.

However, in the present manufacturing method, a large excess of alkali hydroxide and acidic iron salt is added to the fatty acid, and thus, an excessive water soluble salt is produced in the obtained fatty acid iron salt. Specifically, in the reaction system, an excess sodium hydroxide added to the fatty acid, iron chloride, and sodium chloride produced in the double decomposition reaction remain, and furthermore an unreacted sodium hydroxide and an iron chloride react so that a basic iron salt is produced. When these unreacted raw materials and byproducts are dispersed in the thermoplastic resin, for example, there is a problem of causing a dispersion failure due to a high cohesiveness, and there is also a problem that it is not possible to achieve a high purity of the iron soap.

On the other hand, Patent Literature 2 describes a method of manufacturing a trisoap-type long chain fatty acid iron (II), where the method has a characteristic of reacting an iron (II) trialkoxide and a long chain fatty acid, under inert gas atmosphere by an exchange method in presence of aprotic polar solvent.

However, in the present manufacturing method, the reaction is caused by using a large amount of aprotic polar solvents such as tetrahydrofuran, dioxane, and diethylether. Further, for a purpose of increasing the purity of the trisoap-type long chain fatty acid iron (II), a large excess of 3 to 300 parts by mole of long chain fatty acid, preferably 6 to 100 parts by mole thereof, per 1 part by mole of the iron (II) trialkoxide is added for reaction, and thus a large amount of free fatty acids remains in fatty acid iron salt, and a large amount of aprotic polar solvent is used to wash the large amount of free fatty acids. Therefore, there is a problem of giving large stress on the environment by using a large amount of aprotic polar solvent.

CITATION LIST

Patent Literature

[PTL 1] Japanese Unexamined Patent Application Publication No. H6-271499

[PTL 2] Japanese Unexamined Patent Application Publication No. S62-120339

SUMMARY OF THE INVENTION

Technical Problem

An object of the present invention is to provide a method of manufacturing an iron soap which has high compatibility and dispersibility with respect to a thermoplastic resin and which is capable of suitably being used as a dispersant for a photodecomposition catalyst, an inorganic powder or the like. The manufacturing method is able to produce the iron soap in high yields.

Solution to Problem

As a result of a number of extensive researches to solve the above problem, the present inventor found that an iron soap in which the content of free fatty acid, the content of water soluble salts, and a granularity summary value were respectively defined within a predetermined range, had high compatibility and dispersibility with respect to a thermoplastic resin, and was capable of being suitably used as a dispersant for a photodecomposition catalyst, an inorganic powder or the like, and also found that by adjusting the pH obtained when a straight-chain saturated fatty acid alkali metal salt aqueous solution was reacted with a trivalent iron salt aqueous solution, it was possible to obtain the above iron soap.

That is, the present invention is a method of manufacturing an iron soap where a content A (%) of free fatty acid is $0.01 \leq A \leq 8.0$, a content B (%) of water soluble salt is $0.01 \leq B \leq 0.5$ and a granularity summary value C indicated in Formula (1) is $0.1 \leq C \leq 5.0$, wherein the iron soap is a salt of a straight-chain saturated fatty acid having from 12 to 22 carbons and an iron, Granularity summary value $C=(D90-D10)/D50$
(where $1.0 \leq D50 \leq 40.0$)   Formula (1)

D10: 10% cumulative diameter (μm) of fatty acid metal salt particles on a volumetric basis
D50: 50% cumulative diameter (μm) of fatty acid metal salt particles on a volumetric basis
D90: 90% cumulative diameter (μm) of fatty acid metal salt particles on a volumetric basis the method comprising the steps of:
reacting, at a temperature equal to or lower than a crystal transition initiation temperature of the iron soap to be manufactured, between a straight-chain saturated fatty acid alkali metal salt aqueous solution having from 12 to 22 carbons and a trivalent iron salt aqueous solution with pH of 0.1 to 5.5 so as to prepare an iron soap slurry; and
adjusting pH of the prepared iron soap slurry to from 0.1 to 6.0.

Advantageous Effects of Invention

The iron soap of the present invention has high compatibility and dispersibility with respect to a thermoplastic resin, and is capable of suitably being used as a dispersant for a photodecomposition catalyst, an inorganic powder or the like.

Further, the method of manufacturing the iron soap of the present invention enables production of the iron soap of the present invention in high yields.

DETAILED DESCRIPTION OF THE PREFERRED EMBODIMENTS

Embodiments of the present invention will be described, below.

First, an iron soap of the present invention will be described, and a method of manufacturing the iron soap of the present invention by which it is possible to produce the iron soap in high yields, and a thermoplastic resin composition containing the iron soap of the present invention will be described sequentially.

[Iron Soap]

In the iron soap of the present invention, a content A (%) of free fatty acid is $0.01 \leq A \leq 8.0$, preferably $0.01 \leq A \leq 6.0$, and particularly preferably $0.01 \leq A \leq 4.0$. When the content A is too large, upon dispersing the iron soap in a thermoplastic resin, there is a concern that dispersibility may decrease such as a bleedout in the resin. Further, the iron content in the iron soap significantly decreases and a photodecomposition performance of the resin decreases, and thus, there is a concern that the photodecomposition becomes difficult.

It is noted that measurement of the content A (%) of the free fatty acids may be performed by titration using an alkali solution.

In the iron soap of the present invention, a content B (%) of water soluble salt is $0.01 \leq B \leq 0.5$, preferably $0.01 \leq B \leq 0.3$, and particularly preferably $0.01 \leq B \leq 0.2$. When the content B is too large, upon being added to the thermoplastic resin, for example, there is a concern that the dispersibility may decrease due to hygroscopicity of the water soluble salts, for example.

It is noted that the content B of the water soluble salts may be evaluated from a difference in mass when a sample is boiled with water.

In the iron soap of the present invention, the granularity summary value C expressed in Formula (1) is $0.1 \leq C \leq 5.0$, preferably $0.1 \leq C \leq 4.0$, and particularly preferably $0.1 \leq C \leq 3.0$. When the granularity summary value C is too large, upon the iron soap being added to a thermoplastic resin, for example, there is a concern that a uniform dispersibility may be impaired because the granulometric distribution is wide. On the other hand, when the granularity summary value C is too small, the yield is deteriorated and the productivity is lowered, which may be disadvantageous from a viewpoint of cost.

Thus, the iron soap which has a small amount of coarse particles and a specified granulometric distribution, has high dispersibility when being melt-kneaded after being added to the thermoplastic resin, and thus, a great effect as a photodecomposition catalyst is easily obtained.

It is noted that it is possible to calculate the granularity summary value C from a particle size measured by a Microtrac laser diffraction method.

Granularity summary value $C=(D90-D10)/D50$
(where $1.0 \leq D50 \leq 40.0$)   Formula (1)

D10: 10% cumulative diameter (μm) of fatty acid metal salt particles on a volumetric basis
D50: 50% cumulative diameter (μm) of fatty acid metal salt particles on a volumetric basis
D90: 90% cumulative diameter (μm) of fatty acid metal salt particles on a volumetric basis It is noted that the granularity summary value C may be adjusted by properly adjusting the concentration of the fatty acid alkali metal salt, a temperature during the reaction between a fatty acid alkali metal salt aqueous solution and a trivalent iron salt aqueous solution, and a dropping speed when the trivalent iron salt aqueous solution is dropped into the fatty acid alkali metal salt aqueous solution, respectively. Further, when particles with a broad granulometric distribution, in other words, with a large granularity summary value C, are adjusted, these particles may be classified by using sieves with 100 mesh, 200 mesh, 330 mesh, or the like in a post-process.

[Method of Manufacturing Iron Soap]

A method of manufacturing an iron soap of the present invention comprises steps of: preparing an iron soap slurry by mixing a straight-chain saturated fatty acid alkali metal salt aqueous solution and a trivalent iron salt aqueous solution to cause a reaction; and adjusting pH of the prepared iron soap slurry to within a predetermined range.

Examples of the fatty acid salts used to prepare the straight-chain saturated fatty acid alkali metal salt aqueous solution include an alkali metal salt of straight-chain saturated fatty acid having from 12 to 22 carbons. Examples of such fatty acid salts include alkali metal salts such as: sodium and potassium of a simple fatty acid represented by lauric acid, myristic acid, palmitic acid, stearic acid, arachidic acid, behenic acid and the like; or sodium and potassium of a straight chain saturated mixed fatty acids derived from animals and plants represented by tallow fatty acid, lard fatty acid, soybean oil fatty acid, coconut oil fatty acid, palm oil fatty acid and the like. The aforementioned fatty acid salts may be used alone, or two or more types thereof may be used in combination.

When using alkali metal salts of the straight-chain saturated fatty acid having less than 12 carbons, a solubility to water of the obtained iron soap increases, and thus, there is a concern that the yield is significantly lowered. Further, when the fatty acid salts are added to a thermoplastic resin and melt-kneaded by heating, the compatibility becomes lower and the dispersibility may be lowered. On the other hand, when using alkali metal salts of a long straight-chain saturated fatty acid having more than 22 carbons, the solubility to the water is significantly lowered, and thus, it is necessary to significantly lower the concentration of the aqueous solution, which may lead to lowering the productive efficiency.

The content of the straight-chain saturated fatty acid alkali metal salt in the straight-chain saturated fatty acid alkali metal salt aqueous solution is 0.1 to 20 mass %, for example. When the content is too small, the amount of obtained iron soap is significantly small with respect to the amount of reaction solution, and thus, there is a concern that the productive efficiency may be lowered. Further, when the content is too large, the concentration of the iron soap dispersion solution during or after the reaction is too high, causing the reaction to slow down, and there is a concern that the purity of the iron (III) soap may be lowered. When an iron soap having a high iron (III) soap purity is more efficiently manufactured, the content of the alkali metal salt of the fatty acid in the aqueous solution is preferably 1 to 15 mass %, and particularly preferably 3 to 15 mass %.

Examples of the iron salt used to prepare the trivalent iron salt aqueous solution include iron (III) chloride and iron (III) sulfate. The aforementioned compounds may be used alone, or two or more types thereof may be used in combination.

Further, when preparing an iron salt aqueous solution having a predetermined concentration, a predetermined amount of inorganic acid such as hydrochloric acid and sulfuric acid is added to adjust the pH to from 0.1 to 5.5, preferably to from 0.1 to 5.0, and particularly preferably to from 0.5 to 4.0.

The content of the iron salt in the trivalent iron salt aqueous solution is 0.1 to 40 mass %, for example. When the content is too small, the amount of obtained iron soap is significantly small with respect to the amount of reaction solution, and thus, there is a concern that the productive efficiency may be lowered. Further, when the content is too large, the aggregation of obtained iron soap particles easily proceeds, and thus, obtaining a uniform iron soap slurry may become difficult. In order to stably manufacture a uniform iron soap slurry in which the aggregation of the obtained iron soap particles is suppressed, a preferable content of the iron salt in the iron salt aqueous solution is 0.5 to 30 mass %, and a particularly preferable content is 1.0 to 30 mass %.

The reaction between the straight-chain saturated fatty acid alkali metal salt aqueous solution and the trivalent iron salt aqueous solution is preferably conducted while adjusting an equivalent ratio (straight-chain saturated fatty acid alkali metal salt/iron salt) of the straight-chain saturated fatty acid alkali metal salt with respect to the iron salt to be in the range from 0.5 to 3.0, which makes it easy to adjust the pH of the iron soap slurry to from 0.1 to 6.0.

In the present invention, it is necessary to mix the straight-chain saturated fatty acid alkali iron salt aqueous solution and the trivalent iron salt aqueous solution at a temperature equal to or lower than a crystal transition initiation temperature of the iron soap to be manufactured, and cause a reaction.

Here, the crystal transition initiation temperature is a temperature at which the crystal structure of the iron soap begins to change, and for example, in a heat absorption graph by Differential Scanning calorimetry (DSC) of iron (III) stearate, an intersection point between an extension line of a base line before an initiation of the heat absorption and a tangent line at the inflection point of the gradient curve after the initiation of heat absorption is regarded as the crystal transition initiation temperature.

The crystal transition initiation temperature of the iron (III) stearate is 84° C. Further, the crystal transition initiation temperature is 85° C. for an iron (III) behenate, 83° C. for an iron (III) palmitate, 81° C. for an iron (III) myristate, and 79° C. for an iron (III) laurate. Further, for example, the crystal transition initiation temperature is 83° C. for an iron (III) soap prepared with mixed fatty acids in which stearic acid and palmitic acid are mixed at a mass ratio of 65:35.

The reaction between the straight-chain saturated fatty acid alkali metal salt aqueous solution and the trivalent iron salt aqueous solution is preferably conducted at a temperature or higher at which the straight chain fatty acid alkali metal salt aqueous solution is completely dissolved. Specifically, it is preferable to conduct the reaction at a temperature equal to or higher than a temperature lower by 30° C. than the crystal transition initiation temperature of the iron soap to be manufactured. When the iron (III) stearate is manufactured, for example, it is preferable to conduct the reaction at 54° C. or higher.

It is noted that the measurement of the Differential Scanning calorimetry (DSC) is conducted by using a sample of 10 mg, under a nitrogen gas stream (60 ml/min), and at a temperature rising rate of 2° C./min from 0° C. to 150° C.

A reaction temperature at the time of actual mixing of both aqueous solutions differs depending on the fatty acid chain of the obtained iron soap; however, for example, in a case of manufacturing the iron (III) stearate, 60 to 79° C. is preferred and 65 to 75° C. is particularly preferred. When the reaction temperature is too low, the solubility of the alkali metal stearate salt to water in the alkali metal stearate salt aqueous solution decreases, and therefore, although the iron (III) stearate as a target substance may be obtained, the finally obtained amount of the iron soap is lower than the amount of the reaction solution, and the productive efficiency may be lowered. When the reaction temperature is too high, an aggregation and a fusion occur in particles of the iron soap slurry produced during the double decomposition reaction, and not only it is difficult to obtain the iron soap of fine particles, but also there is a concern that a large amount of fatty acid alkali metal salt aggregates and fuses together and remains inside the iron soap.

The iron soap slurry is obtained by the method described above. The iron soap slurry is used as it is, or a solvent thereof is separated by a centrifugal extractor, a filter press, a vacuum rotary filter, or the like. Further the iron soap slurry is washed, if necessary, to remove the byproduct inorganic salt, and then is dried by a rotary dryer, an airborne dryer, a ventilating dryer, a spray dryer, a fluid bed dryer, or the like. The drying method may be continuous or batch type, or either under normal pressure or vacuum.

Further, the dried iron soap is disintegrated as necessary. The disintegration method is not particularly limited, and the disintegration may be done with a pin mill, a jet mill, or an atomizer, for example. The disintegrated iron soap particles are classified. That is, the particles are classified with, for example, a multi-stage sieve device for sieving particles with vibrations, or the like for adjusting a granulometric distribution. Thus, the iron soap particles can be obtained which are easily melted and dispersed into a thermoplastic resin, and of which the content of each of the free fatty acid and the water soluble salt is small and the granularity summary value is within a predetermined range.

The pH of the iron soap slurry obtained in the present invention is adjusted to from 0.1 to 6.0, preferably to from 0.1 to 4.0. When the pH of the iron soap slurry is too high, it is difficult to obtain an iron (III) soap having 3 mol of fatty acids bonded per 1 mol of iron, causing partial hydrolysis, and thus, there is a concern that an iron soap (disoap) is produced in which 2 mol of fatty acids are bonded per 1 mol of iron. On the other hand, when the pH of the iron soap slurry is too low, the obtained iron soap is easily decomposed, and thus, there is a concern of having excessive amount of free fatty acid.

It is noted that it is preferable that after obtaining the iron soap slurry, the slurry is aged for 10 minutes to 2 hours in a state in which the reaction temperature and the pH of the iron soap slurry are maintained within the above-mentioned range.

[Thermoplastic Resin Composition]

It is preferable that the iron soap of the present invention is contained in a thermoplastic resin and used for a purpose of decomposing the thermoplastic resin.

The thermoplastic resin composition of the present invention contains a thermoplastic resin and an iron soap of the present invention. The above-mentioned thermoplastic resin may be either a non-polar resin or a polar resin, and examples thereof may include polyurethane, polystyrene, and polyolefin; examples of the polyolefin include polypropylene, low density polyethylene, and high density polyethylene. Further, examples of the thermoplastic resin may also include ethylene/vinyl acetate copolymer, ethylene/vinyl alcohol copolymer, ethylene/methyl acrylate copolymer, and polymethylmethacrylate. It is possible to obtain the thermoplastic resin composition of the present invention by melting and mixing the iron soap with the thermoplastic resin under a heating condition.

The content of iron soap in the thermoplastic resin composition of the present invention is preferably from 0.01 to 10 parts by mass per 100 parts by mass of thermoplastic resin, and more preferably from 0.1 to 8 parts by mass. When the content of iron soap is too small, a property of the iron soap is difficult to maintain, and when the content is too large, the thermoplastic resin is easily and significantly deteriorated.

As a dispersion aid to highly disperse the iron soap in the thermoplastic resin, a fatty acid calcium soap, that which is preferably obtained by a double decomposition method, is used appropriately. Specifically, examples thereof may include calcium laurate, calcium myristate, calcium palmitate, calcium stearate, and calcium behenate, and the calcium stearate is preferable. Below, the fatty acid calcium soap obtained by the double decomposition method is also referred to as a double decomposed fatty acid calcium soap.

The amount of double decomposed fatty acid calcium soap to be added to the iron soap is preferably from 0.01 to 100 parts by mass per 100 parts by mass of iron soap, and more preferably from 0.1 to 100 parts by mass. When the addition amount of the double decomposed fatty acid calcium soap is too small, it becomes difficult to obtain a property to improve dispersibility of the iron soap. On the other hand, if the addition amount is too large, it becomes difficult to obtain a function as a dispersant for a photodecomposition catalyst, an inorganic powder or the like of the iron soap in the thermoplastic resin.

As the double decomposed fatty acid calcium soap, it is preferable that the granularity summary value C of Formula (1) is $C \leq 2.0$, and in the double decomposed fatty acid calcium soap (fatty acid metal salt particles) which has been left in an environment of 80° C. for 10 minutes, the aggregation degree E (%) of Formula (2) measured by a powder tester is $E \leq 20$.

The double decomposed fatty acid calcium soap satisfying the above-mentioned values, improves the dispersibility and coatability on the iron soap, thus more significantly contributing to the improvement of dispersibility when added to the thermoplastic resin.

$$\text{Aggregation degree } E = [(\text{mass of fatty acid metal salt particles remaining on a sieve with a mesh size of } 350\ \mu m)/2] \times 100 \times (1/1) + [(\text{mass of fatty acid metal salt particles remaining on a sieve with a mesh size of } 250\ \mu m)/2] \times 100 \times (3/5) + [(\text{mass of fatty acid metal salt particles remaining on a sieve with a mesh size of } 150\ \mu m)/2] \times 100 \times (1/5)] \quad \text{Formula (2)}$$

EXAMPLES

The present invention will be more specifically described by using Examples and Comparative Examples below.

It is noted that in the following Examples and the Comparative Examples, the pH of the slurry (dispersion solution), a content A (%) of free fatty acid, a content B (%) of water soluble salt, and a granularity summary value C were measured as follows: The results were compiled in Table 1.

1) pH of the Slurry (Dispersion Solution):

20 g of the iron soap slurry was weighed and placed in a 200-ml beaker. The pH was measured while stirring so that the soap slurry became uniform.

2) Content a (%) of the Free Fatty Acid:

5 g of the iron soap was weighed and placed in a beaker, 50 g of diethylether-ethanol mixed solvent (1:1) was added thereto, after being stirred for 30 seconds, the mixture was left to stand for 30 minutes. Thereafter, the mixture was filtered using a 5B filter paper, the filtrate was titrated by using the N/10 potassium hydroxide titration solution, and the amount of free fatty acid was calculated according to the following formula. The similar operation was also performed for the blank fatty acid.

$$\text{Content of free fatty acid} = (VA - VB) \times f \times M / W / 100$$

where

VA: Dropping amount in the sample (ml)
VB: Dropping amount in the blank (ml)
f: factor of N/10 potassium hydroxide titration solution
M: molecular weight of fatty acid used
W: amount of iron soap sample (g)

3) Content B (%) of the Water Soluble Salt:

2 g of the iron soap is weighed and placed in an Erlenmeyer flask, and after 50 g of water is added, an air cooling tube is attached to the flask for boiling for one hour while shaking on a water bath. Then, the solution is filtered using filter paper into a 100-ml beaker. 10 ml of water is added to the residue in the Erlenmeyer flask, then the filtration process is repeated three times. After volatilizing water in the 100-ml beaker on the water bath, the beaker is dried for one hour in a constant-temperature dryer at 105±2° C., and after cooling down in the desiccator, the content is weighed.

Content $B$ (%) of water soluble salt=[residue (g)/ collected sample amount (g)]×100

4) Granularity Summary Value C:
Granularity (D10, D50, D90);

A granulometric distribution measuring instrument (equipment name "Microtrac MT-3000" manufactured by NIKKISO Co., Ltd.) was used for measurement (Principle: laser diffraction-scattering method).

A cumulative curve was drawn with the whole volume of a cluster of powders to be measured as 100%, and particles sizes at the 10%, 50%, and 90% points of the cumulative curve were obtained as 10% diameter (D10), 50% diameter (D50), and 90% diameter (D90) (μm) respectively.

Granularity summary value $C=(D90-D10)/D50$
(where $1.0 \leq D50 \leq 40.0$)     Formula (1)

D10: 10% cumulative diameter (μm) of fatty acid metal salt particles on a volumetric basis
D50: 50% cumulative diameter (μm) of fatty acid metal salt particles on a volumetric basis
D90: 90% cumulative diameter (μm) of fatty acid metal salt particles on a volumetric basis Example 1

250 g of stearic acid (neutralization value of 203 mg KOH/g) and 2700 g of water were prepared into a 5 L separable flask, and heated up to 60° C. Subsequently, 75.4 g of 48 mass % sodium hydroxide aqueous solution was added thereto, and then the mixture was stirred for one hour at the same temperature (60° C.), and thus, the fatty acid alkali metal salt aqueous solution was obtained.

Then, while maintaining the solution at 60° C., 506.4 g of 25% iron (III) sulfate aqueous solution [$Fe_2(SO_4)_3$ aqueous solution] in which the pH was adjusted to 0.63 by adding a titration amount of sulfuric acid (reagent), was dropped to the fatty acid alkali metal salt aqueous solution for 40 minutes, thus the pH of the iron soap slurry became 1.4.

After the dropping was completed, the solution was stirred for 10 minutes while maintaining the solution at 60° C. for aging. 1500 g of water was added to the obtained aqueous dispersion slurry of the iron stearate soap, which was followed by cooling to 50° C. or lower. Then the mixture was filtered with a suction filter and was washed with 1000 g of water twice. The obtained cake was dried and ground by a micron dryer, and thus, iron stearate soap particles in powder form were obtained.

Example 2

250 g of stearic acid (neutralization value of 203 mg KOH/g) and 2700 g of water were prepared into a 5 L separable flask, and heated up to 65° C. Subsequently, 75.4 g of 48 mass % sodium hydroxide aqueous solution was added thereto, and then the mixture was stirred for one hour at the same temperature (65° C.), and thus, the fatty acid alkali metal salt aqueous solution was obtained.

Then, while maintaining the solution at 65° C., 506.4 g of 25% iron (III) sulfate aqueous solution [$Fe_2(SO_4)_3$ aqueous solution] in which the pH was adjusted to 1.7 by adding a titration amount of sulfuric acid (reagent), was dropped to the fatty acid alkali metal salt aqueous solution for 40 minutes, thus the pH of the iron soap slurry became 2.0.

After the dropping was completed, the solution was stirred for 10 minutes while maintaining the solution at 65° C. for aging. 1500 g of water was added to the obtained aqueous dispersion slurry of the iron stearate soap, which was followed by cooling to 50° C. or lower. Then the mixture was filtered with a suction filter and was washed with 1000 g of water twice. The obtained cake was dried and ground by a micron dryer, and thus, iron stearate soap particles in powder form were obtained.

Example 3

250 g of palmitic acid (neutralization value of 219 mg KOH/g) and 2700 g of water were prepared into a 5 L separable flask, and heated up to 65° C. Subsequently, 81.3 g of 48 mass % sodium hydroxide aqueous solution was added thereto, and then the mixture was stirred for one hour at the same temperature (65° C.), and thus, the fatty acid alkali metal salt aqueous solution was obtained.

Then, while maintaining the solution at 65° C., 546.3 g of 25% iron (III) sulfate aqueous solution [$Fe_2(SO_4)_3$ aqueous solution] in which the pH was adjusted to 2.2 by adding a titration amount of sulfuric acid (reagent), was dropped to the fatty acid alkali metal salt aqueous solution for 60 minutes, thus the pH of the iron soap slurry became 2.4.

After the dropping was completed, the solution was stirred for 20 minutes while maintaining the solution at 65° C. for aging. 1500 g of water was added to the aqueous dispersion slurry of the obtained iron palmitate soap, which was followed by cooling to 50° C. or lower. Then, the mixture was filtered with a suction filter and washed with 1000 g of water twice. The obtained cake was dried and ground by a micron dryer, and thus, iron palmitate soap particles in powder form were obtained.

Example 4

250 g of stearic acid (neutralization value of 208 mg KOH/g) and 2700 g of water were prepared into a 3 L separable flask, and heated up to 65° C. Subsequently, 77.2 g of 48 mass % sodium hydroxide aqueous solution was added thereto, and then the mixture was stirred for one hour at the same temperature (65° C.), and thus, the fatty acid alkali metal salt aqueous solution was obtained.

Then, while maintaining the solution at 65° C., 210.4 g of 25% iron (III) chloride aqueous solution [$FeCl_3$ aqueous solution] in which the pH was adjusted to 3.6 by adding a titration amount of hydrochloric acid (reagent), was dropped to the fatty acid alkali metal salt aqueous solution for 40 minutes, thus the pH of the iron soap slurry became 3.8.

After the dropping was completed, the solution was stirred for 20 minutes while maintaining the solution at 65° C. for aging. 1500 g of water was added to the obtained aqueous dispersion slurry of the iron stearate soap, which was followed by cooling to 50° C. or lower. Then the mixture was filtered with a suction filter and was washed with 1000 g of water twice. The obtained cake was dried and ground by a micron dryer, and thus, iron stearate soap particles in powder form were obtained.

Example 5

250 g of stearic acid (neutralization value of 203 mg KOH/g) and 2700 g of water were prepared into a 3 L separable flask, and heated up to 70° C. Subsequently, 75.3 g of 48 mass % sodium hydroxide aqueous solution was added thereto, and then the mixture was stirred for one hour at the same temperature (70° C.), and thus, the fatty acid alkali metal salt aqueous solution was obtained.

Then, while maintaining the solution at 70° C., 205.4 g of 25% iron (III) chloride aqueous solution [$FeCl_3$ aqueous solution] in which the pH was adjusted to 2.5 by adding a titration amount of hydrochloric acid (reagent), was dropped to the fatty acid alkali metal salt aqueous solution for 60 minutes, thus the pH of the iron soap slurry became 2.9.

After the dropping was completed, the solution was stirred for 20 minutes while maintaining the solution at 70° C. for aging. 1500 g of water was added to the obtained aqueous dispersion slurry of the iron stearate soap, which was followed by cooling to 50° C. or lower. Then the mixture was filtered with a suction filter and was washed with 1000 g of water twice. The obtained cake was dried and ground by a micron dryer, and thus, iron stearate soap particles in powder form were obtained.

Comparative Example 1

A reagent of an iron (III) stearate manufactured by Kishida Chemical Co., Ltd. was used.

Comparative Example 2

250 g of stearic acid (neutralization value of 203 mg KOH/g) and 2700 g of water were prepared into a 5 L separable flask, and heated up to 85° C. Subsequently, 77.2 g of 48 mass % sodium hydroxide aqueous solution was added thereto, and then the mixture was stirred for one hour at the same temperature (85° C.), and thus, the fatty acid alkali metal salt aqueous solution was obtained.

Then, while maintaining the solution at 85° C., 506.4 g of 25% iron (III) sulfate aqueous solution [$Fe_2(SO_4)_3$ aqueous solution] in which the pH was adjusted to 1.8 by adding a titration amount of sulfuric acid (reagent), was dropped to the fatty acid alkali metal salt aqueous solution for 40 minutes, thus the pH of the iron soap slurry became 2.7.

After the dropping was completed, the solution was stirred for 20 minutes while maintaining the solution at 85° C. for aging. 1500 g of water was added to the obtained block-shaped iron stearate soap, which was followed by cooling to 50° C. or lower. Then, the mixture was filtered with a suction filter and washed with 1000 g of water twice. The obtained block-shaped soap was dried using a shelf and ground by a mixer, and thus, iron stearate soap particles in granular form were obtained.

Comparative Example 3

250 g of stearic acid (neutralization value of 203 mg KOH/g) and 2700 g of water were prepared into a 3 L separable flask, and heated up to 90° C. Subsequently, 77.2 g of 48 mass % sodium hydroxide aqueous solution was added thereto, and then the mixture was stirred for one hour at the same temperature (90° C.), and thus, the fatty acid alkali metal salt aqueous solution was obtained.

Then, while maintaining the solution at 90° C., 506.4 g of 25% iron (III) sulfate aqueous solution [$Fe_2(SO_4)_3$ aqueous solution] in which the pH was adjusted to 2.3 by adding a titration amount of sulfuric acid (reagent), was dropped to the fatty acid alkali metal salt aqueous solution for 40 minutes, thus the pH of the iron soap slurry became 1.6.

After the dropping was completed, the solution was stirred for 20 minutes while maintaining the solution at 90° C. for aging. 1500 g of water was added to the obtained block-shaped iron stearate soap, which was followed by cooling to 50° C. or lower. Then, the mixture was filtered with a suction filter and washed with 1000 g of water twice. The obtained block-shaped soap was dried using a shelf and ground by a mixer, and thus, iron stearate soap particles in granular form were obtained.

Comparative Example 4

250 g of stearic acid (neutralization value of 208 mg KOH/g) and 2700 g of water were prepared into a 3 L separable flask, and heated up to 70° C. Subsequently, 77.2 g of 48 mass % sodium hydroxide aqueous solution was added thereto, and then the mixture was stirred for one hour at the same temperature (70° C.), and thus, the fatty acid alkali metal salt aqueous solution was obtained.

Then, while maintaining the solution at 70° C., 506.4 g of 25% iron (III) sulfate aqueous solution [$Fe_2(SO_4)_3$ aqueous solution] in which the pH was adjusted to 5.3 by adding a titration amount of sulfuric acid (reagent), was dropped to the fatty acid alkali metal salt aqueous solution for 40 minutes, thus the pH of the iron soap slurry became 6.4.

After the dropping was completed, the solution was stirred for 20 minutes while maintaining the solution at 70° C. for aging. 1500 g of water was added to the obtained aqueous dispersion slurry of the iron stearate soap, which was followed by cooling to 50° C. or lower. Then the mixture was filtered with a suction filter and was washed with 1000 g of water twice. The obtained cake was dried and ground by a micron dryer, and thus, iron stearate soap particles in powder form were obtained.

Comparative Example 5

Synthesis of the Iron Stearate was Carried Out in Accordance with Example 1 of Patent Literature 1.

In a 2 L beaker, 75 g of stearic acid (NV=204; neutralizing value) was added to 500 g of sodium hydroxide (reagent, special grade) aqueous solution, which was heat to 90° C. and stirred up, to saponify the stearic acid to obtain a transparent rubber form of sodium stearate.

Next, 222 ml of 0.4 M iron (III) chloride aqueous solution was slowly added to the reaction mixture and the double decomposition reaction was carried out. After obtaining a suspended red product, water contained in the reaction solution was filtered out thus completed the initial synthesis reaction.

Thereafter, 156 ml of 0.4 M sodium hydroxide aqueous solution and 344 ml of purified water were added to the reaction solution, which were heat to 90° C. and stirred to saponify the stearic acid remaining in the product. Thereafter, 55 ml of 0.4 M iron (III) chloride aqueous solution was further added, producing suspended iron stearate, followed by addition of 93.6 ml of 0.4M sodium hydroxide aqueous solution to carry out a saponification reaction with the remaining stearic acid. After this, 33 ml of 0.4 M iron (III) chloride aqueous solution was added to carry out the double decomposition reaction. Then, after the saponification reaction by further adding 50 ml of 0.4 M sodium hydroxide aqueous solution, 18 ml of 0.4 M iron (III) chloride aqueous solution was added, which resulted in the iron (III) stearate of the target product. Then the mixture was filtered with a suction filter and was washed with 1000 g of water twice. The obtained cake was dried and ground by a micron dryer, and thus, iron stearate soap particles in powder form were obtained.

TABLE 1

| | | Slurry pH | Free fatty acid A (%) | Water soluble salt B (%) | D50 (μm) | Granularity summary value C (μm) |
|---|---|---|---|---|---|---|
| Example 1 | Iron (III) stearate prototype 1 | 1.4 | 2.1 | 0.19 | 6.8 | 1.9 |
| Example 2 | Iron (III) stearate prototype 2 | 2.0 | 1.4 | 0.08 | 5.4 | 1.4 |
| Example 3 | Iron (III) palmitate prototype 3 | 2.4 | 1.6 | 0.14 | 6.2 | 2.5 |
| Example 4 | Iron (III) stearate prototype 4 | 3.8 | 1.9 | 0.20 | 5.8 | 2.1 |
| Example 5 | Iron (III) stearate prototype 5 | 2.9 | 2.7 | 0.24 | 9.8 | 2.9 |
| Comparative Example 1 | Iron (III) stearate reagent | No data | 8.7 | 0.98 | 34.5 | 5.7 |
| Comparative Example 2 | Iron (III) stearate prototype 6 | 2.7 | 15.7 | 4.72 | 245.1 | 7.5 |
| Comparative Example 3 | Iron (III) stearate prototype 7 | 1.6 | 23.8 | 6.31 | 368.2 | 8.1 |
| Comparative Example 4 | Iron (III) stearate prototype 8 | 6.4 | 8.9 | 1.08 | 8.7 | 2.7 |
| Comparative Example 5 | Iron (III) stearate prototype 9 | 8.2 | 3.9 | 2.89 | 12.4 | 6.6 |

Next, 3.2 g of each of 10 types of iron (III) soap particles as shown in Table 1 evaluated in the above Examples and Comparative Examples was used to be kneaded with 60.0 g of non-additive low density polyethylene (MIRASON 16P, manufactured by Prime Polymer Co., Ltd.) for five minutes under a temperature of 180° C. by a biaxial kneader (Laboplastomill), which was followed by being formed into a 1 mm thick sheet by hot pressing.

Example 6

3.2 g of the iron (III) stearate soap particles obtained in Example 1 was processed in much the same way as above except for using a composition added with 0.32 g of calcium stearate obtained by the double decomposition method having the granularity summary value C of 1.8 and the aggregation degree E of 12.5%, resulting in a sheet having a thickness of 1 mm being formed.

The obtained sheet was evaluated as follows.

[Overall Grade of Whiteness and Clarity]

For the obtained sheet, whiteness (WI) and lightness (L) were measured by using Z-100DP colormeter manufactured by Nippon Denshoku Industries Co., Ltd., and determined in five grades.

It is noted that the measurement was performed by arbitrarily selecting five locations. Here, a first grade is when the clarity and whiteness are the highest, and a fifth grade is when the clarity and whiteness are the lowest. The grade determination results are shown in Table 2 below.

[MFR Value]

For the obtained sheet, irradiation test was carried out by using a deterioration acceleration testing machine, EYE Super SUV-W161 type (manufactured by Iwasaki Electric Co., Ltd.). The sheet was irradiated with a UV illuminance of 150 mW/cm$^2$ for 60 hours. After the test, the sheet was cut finely and a melt mass flow rate (MFR, unit: g/10 min) value was measured five times under the condition of a load of 21.18N and a temperature of 190° C. in accordance with a method specified by JIS K7210-1995.

TABLE 2

| | | Overall Grade of Whiteness and Clarity | MFR value (g/10 min) | |
|---|---|---|---|---|
| | | Average value | Average value | Standard deviation |
| Example 1 | Iron (III) stearate prototype 1 | 1 | 3.4 | 0.08 |
| Example 2 | Iron (III) stearate prototype 2 | 1 | 3.6 | 0.11 |
| Example 3 | Iron (III) palmitate prototype 3 | 1 | 3.2 | 0.05 |
| Example 4 | Iron (III) stearate prototype 4 | 1 | 3.2 | 0.07 |
| Example 5 | Iron (III) stearate prototype 5 | 2 | 3.0 | 0.05 |
| Example 6 | Iron (III) stearate prototype 1 + Calcium stearate | 1 | 3.9 | 0.07 |
| Comparative Example 1 | Iron (III) stearate reagent | 4 | 2.7 | 0.08 |
| Comparative Example 2 | Iron (III) stearate prototype 6 | 5 | 2.4 | 0.16 |
| Comparative Example 3 | Iron (III) stearate prototype 7 | 5 | 2.3 | 0.22 |
| Comparative Example 4 | Iron (III) stearate prototype 8 | 3 | 2.7 | 0.05 |
| Comparative Example 5 | Iron (III) stearate prototype 9 | 3 | 2.5 | 0.15 |

In Examples 1 to 5, by reacting the fatty acid alkali metal salt aqueous solution and the iron salt aqueous solution under the conditions of the temperature and pH specified in the present invention, iron soap particles having the content A of the free fatty acid, the content B of the water soluble salt, and the granularity summary value C specified in the present invention are obtained. Further, when the iron soap particles of Examples 1 to 5 are added to the low density polyethylene which is a thermoplastic resin, the overall grade was good, and improvement of fluidity (MFR value) due to acceleration of decomposition of polyethylene was obtained.

Further, in Example 6, due to combination with calcium stearate from the double decomposition method, dispersibility of iron soap particles further improved, and a higher improvement of fluidity was observed.

On the other hand, when the reagent of iron (III) stearate (manufactured by Kishida Chemical Co., Ltd.) in Comparative Example 1, having a large content A of free fatty acid, was added to the polyethylene, the overall grade became bad, thus improvement of fluidity (MFR value) due to acceleration of decomposition of polyethylene was not obtained.

In iron (III) stearate prototypes 6 and 7 in Comparative Example 2 and Comparative Example 3, the double decomposition reaction was carried out at a higher temperature than a crystal transition initiation temperature, thus the obtained iron soap aggregated and united during the production of slurry, causing instability, where unreacted fatty acids were incorporated, thus the free fatty acid was significantly higher. Further, the iron soap became granular form and the granularity also became coarse, thus the dispersibility significantly deteriorated and high fluidity could not be obtained even with MFR, and variation of numerical value also increased.

When an iron (III) stearate prototype 8 in Comparative Example 4, having a large content A of free fatty acid, was added to the polyethylene, the overall grade became bad, thus improvement in fluidity (MFR value) due to acceleration of decomposition of polyethylene was not obtained.

When an iron (III) stearate prototype 9 of in Comparative Example 5, having a large content B (%) of water soluble salt, was added to the polyethylene, the overall grade became bad, thus improvement in fluidity (MFR value) due to acceleration of decomposition of polyethylene was not obtained.

What is claimed is:

1. A method of manufacturing an iron soap having a content A (%) of free fatty acid being $0.01 \leq A \leq 8.0$, a content B (%) of water soluble salt being $0.01 \leq B \leq 0.5$, and a granularity summary value C indicated in Formula (1) being $0.1 \leq C \leq 5.0$, wherein the iron soap is a salt of a straight-chain saturated fatty acid having from 12 to 22 carbons and an iron, $$\text{Granularity summary value } C = (D90 - D10)/D50 \quad \text{(where } 1.0 \leq D50 \leq 40.0\text{)} \quad \text{Formula (1)}$$

D10: 10% cumulative diameter (μm) of fatty acid metal salt particles on a volumetric basis
D50: 50% cumulative diameter (μm) of fatty acid metal salt particles on a volumetric basis
D90: 90% cumulative diameter (μm) of fatty acid metal salt particles on a volumetric basis
the method comprising the steps of:
reacting, at a temperature equal to or lower than a crystal transition initiation temperature of the iron soap to be manufactured, between a straight-chain saturated fatty acid alkali metal salt aqueous solution having from 12 to 22 carbons and a trivalent iron salt aqueous solution with pH of 0.1 to 5.5 so as to prepare an iron soap slurry; and
adjusting pH of the prepared iron soap slurry to from 0.1 to 6.0.

* * * * *